United States Patent
Weiger et al.

(10) Patent No.: US 9,757,014 B2
(45) Date of Patent: Sep. 12, 2017

(54) ENDOSCOPE WITH ADJUSTABLE VIEWING ANGLE

(75) Inventors: Ulrich Weiger, Kolbingen (DE); Doris Leibinger, Mahlstetten (DE)

(73) Assignee: Karl Storz GmbH & Co. KG, Tuttlingen (DE)

(*) Notice: Subject to any disclaimer, the term of this patent is extended or adjusted under 35 U.S.C. 154(b) by 115 days.

(21) Appl. No.: 13/198,423

(22) Filed: Aug. 4, 2011

(65) Prior Publication Data

US 2012/0035420 A1 Feb. 9, 2012

(30) Foreign Application Priority Data

Aug. 4, 2010 (DE) .................. 10 2010 033 425

(51) Int. Cl.
| | | |
|---|---|---|
| *A61B 1/06* | (2006.01) | |
| *A61B 1/00* | (2006.01) | |
| *G02B 23/24* | (2006.01) | |
| *G02B 26/10* | (2006.01) | |

(52) U.S. Cl.
CPC ...... *A61B 1/00163* (2013.01); *A61B 1/00183* (2013.01); *G02B 23/2423* (2013.01); *G02B 26/108* (2013.01)

(58) Field of Classification Search
CPC ............ A61B 1/00183; A61B 1/00096; A61B 1/00163; G02B 23/243; G02B 26/08
USPC .................. 600/170, 74–75, 173–175, 179; 359/201.1, 203.1, 207.8, 211.1, 211.2, 359/211.3, 211.5, 833; 4/170, 173–175, 4/179
See application file for complete search history.

(56) References Cited

U.S. PATENT DOCUMENTS

| | | | |
|---|---|---|---|
| 5,912,764 A | 6/1999 | Togino | |
| 6,560,013 B1* | 5/2003 | Ramsbottom | G02B 23/243 359/362 |
| 6,692,430 B2* | 2/2004 | Adler | A61B 1/00082 600/108 |
| 7,221,522 B2* | 5/2007 | Tesar et al. | 359/740 |
| 7,564,478 B2* | 7/2009 | Baumann et al. | 348/146 |
| 2003/0076436 A1* | 4/2003 | Otake | G02B 13/007 348/335 |
| 2003/0092966 A1 | 5/2003 | Schara et al. | |

(Continued)

FOREIGN PATENT DOCUMENTS

| | | |
|---|---|---|
| DE | 60015375 T2 | 2/2006 |
| DE | 102005056560 A1 | 12/2006 |

(Continued)

OTHER PUBLICATIONS

German Search Report; Application No. DE 10 2010 033 425.1; Issued: Apr. 11, 2011; 3 pages.

(Continued)

*Primary Examiner* — Alexandra Newton
(74) *Attorney, Agent, or Firm* — Whitmyer IP Group LLC

(57) ABSTRACT

An endoscope with adjustable viewing angle includes a pivotable prism (to divert light that can pivot around a pivot axis to adjust the viewing angle and a fixed prism to divert light that is diverted by the pivotable prism into a direction parallel to the longitudinal axis of the endoscope, such that at least either a light outlet surface of the pivotable prism is positioned in a recess of the fixed prism or a light inlet surface of the fixed prism is positioned in a recess of the pivotable prism.

18 Claims, 3 Drawing Sheets

(56) References Cited

U.S. PATENT DOCUMENTS

2005/0267328 A1* 12/2005 Blumzvig .......... A61B 1/00096
                                                    600/109
2009/0161235 A1*  6/2009 Border et al. ................ 359/726

FOREIGN PATENT DOCUMENTS

| EP | 1586195 B1 | 5/2006 |
| GB | 2354836 A | 4/2001 |
| WO | 2004066614 A1 | 8/2004 |

OTHER PUBLICATIONS

European Search Report: Application No. EP 11 17 6122; Issued: Nov. 28, 2011; Mailing Date: Dec. 6, 2011; 8 pages.

\* cited by examiner

ENDOSCOPE WITH ADJUSTABLE VIEWING ANGLE

CROSS-REFERENCE TO RELATED APPLICATIONS

The present application claims priority of German patent application No. 10 2010 033 425.1 on Aug. 4, 2010.

FIELD OF THE INVENTION

The present invention relates to an endoscope with adjustable viewing angle and a method for recording an image by means of an endoscope.

BACKGROUND OF THE INVENTION

Along with endoscopes for medical and non-medical technical applications, whose viewing angle is parallel to the longitudinal axis of the endoscope shaft, endoscopes with other fixed viewing angles were developed from an early date. Here and throughout the present document, the viewing angle of an endoscope is always understood to mean the direction looking outward from the distal end of the endoscope, that is, the direction in which an object is situated that appears in the center of the image recorded by means of the endoscope. With many applications, however, a fixed viewing angle is a disadvantage. In the most unfavorable case, for example, the endoscope must be replaced repeatedly during a medical procedure. In such cases it is advantageous to use an endoscope with a viewing angle that can be adjusted and/or displaced in situ.

A swing prism endoscope comprises on its distal end a pivotable prism on whose border surfaces light falling into the endoscope is refracted and reflected before it is conveyed, by means of a rod lens system for example, to the proximal end of the endoscope. By pivoting the prism around an axis perpendicular to the longitudinal axis of the endoscope shaft, the viewing angle can be adjusted.

In conventional swing prism endoscopes, the viewing angle range, instantaneous field of view, brightness and image quality are often unsatisfactory. If the viewing angle range is intended to include a viewing direction parallel to the axis of the endoscope shaft (0 degree), for a long time it was only possible to achieve a small viewing angle range. To date, it was not possible to achieve a large viewing angle range whose extreme viewing angles encompass 120 degrees or more.

Patent DE 600 15 375 T2 describes an endoscope with variable viewing angle, which includes two right-angle prisms. One of the right-angle prisms can rotate about an axis of rotation that is orthogonal to the longitudinal axis of the endoscope and intersects it.

SUMMARY OF THE INVENTION

It is an object of the present invention to produce an improved endoscope with adjustable viewing angle and an improved method for recording an image by means of an endoscope.

This object is achieved through the contents of the independent claims.

Refinements are indicated in the dependent claims.

An endoscope with adjustable viewing angle includes a pivotable prism to divert light that can pivot around a pivot axis to adjust the viewing angle, and a fixed prism to divert light that is diverted by the pivotable prism, into a direction parallel to the longitudinal axis of the endoscope, such that at least either a light outlet surface of the pivotable prism is positioned in a recess of the fixed prism or a light inlet surface of the fixed prism is positioned in a recess of the pivotable prism.

A recess in a prism includes in particular a concave portion of the surface of the prism, such that the concave portion can comprise level or locally convex partial areas. A portion of the surface of the prism is, in particular, designated as concave if the surface is concave in the aforementioned sense in a cross-section along a sectional plane, such that the sectional plane in particular includes the optical axis distally and proximally from the reflecting surface.

An object is designated here and hereinafter as convex when its surface is vaulted toward the outside or level. A portion of a surface of a body is designated as convex if the portion of the surface is vaulted toward the outside. A portion of a surface of a body is designated as concave if the portion of the surface is vaulted toward the inside. A portion of an edge of a cross-section surface is designated as convex if the portion of the edge is vaulted toward the outside, and as concave if it is vaulted toward the inside.

The optical axis in the case of a rotation-symmetrical optical system is the axis of symmetry of the optical system. To the extent that endoscopes described here comprise rotation-symmetrical optical components, for example a rod lens system, the optical axis is unequivocally constituted in each case by their axis of symmetry. In certain cases a rotation symmetry is disturbed, but always by prisms. Even when the light outlet surface of the fixed prism is likewise rotation symmetrical to the optical axis of a rod lens system adjoining it downstream in the light flux, the prism inevitably disturbs the rotation symmetry because of its light-diverting property.

If an endoscope described here comprises rotation-symmetrical optical components, then in the location where the rotation symmetry is disturbed, in particular by the prisms, the line that is designated as optical axis is the one in which, in the image of the geometrical lens, a light beam is situated that is located in the rotation-symmetrical optical components in their axis of symmetry. In particular, a light beam running along the optical axis falls on the center of an image sensor of the endoscope or of a video camera coupled with the endoscope.

If an endoscope described here comprises no rotation-symmetrical optical components, or if the definition provided above for the term "optical axis" is not applicable for other reasons, then as optical axis a line is designated, in particular, along which, in the image of the geometrical lens, a light beam runs that is situated at an image point in the center of an image recorded by means of the endoscope. The image recorded by means of the endoscope can be acquired by a video camera or by the human eye at an eyepiece of the endoscope. In particular, the optical axis runs in the center or close to the center of the optical components of the endoscope.

Contrary to the situation in a purely rotation-symmetrical optical system, the optical axis in any case does not therefore primarily comprise the shape of a straight line. At least as long as the refractive index changes only intermittently between two media and not also continually within one medium, the optical axis on the contrary is in part straight. For example, the optical axis comprises three straight portions, that is, a distal portion distally or upstream in the light flux from the pivotable prism, a proximal portion proximally or downstream in the light flux from the fixed prism, and a center portion between the two prisms. At least when the light inlet surfaces and the light outlet surfaces of the prisms are each rotation symmetrical to the optical axis, the optical axis comprises exactly three straight portions that are continuous with one another at reflecting surfaces of the prism.

When the light outlet surface of the pivotable prism is arranged in a recess of the fixed prism, the light inlet surface of the fixed prism forms a part of the surface of the fixed prism that lies inside the recess. When the light inlet surface of the fixed prism is arranged in a recess of the pivotable prism, the light outlet surface of the pivotable prism forms a part of the surface of the pivotable prism that lies inside the recess.

The described arrangement with the light outlet surface of the pivotable prism and the light inlet surface of the fixed prism in or at a recess of the fixed prism and/or of the light outlet surface of the pivotable prism and of the light inlet surface of the fixed prism, and with the light inlet surface of the fixed prism in or at a recess of the pivotable prism, can make possible an especially compact structure of both prisms. It is thereby possible to achieve an especially small distance between the reflecting surfaces of the prisms and an especially small lateral displacement between a distal portion of the optical axis distally from the pivotable prism and the proximal portion of the optical axis proximally from the fixed prism. This is especially true when the reflecting surfaces of the prisms are of different sizes and/or when the light bundle comprises a tapering in the area of the pivotable prism and/or in the area of the fixed prism. Because of a small lateral displacement, with a given cross-section of the endoscope shaft it becomes possible to have especially large cross-sections of rod lenses or other devices to transmit light in the shaft of the endoscope with a simultaneously central or not excessively eccentric arrangement of the light inlet at the distal end of the endoscope.

The pivotable prism in particular is configured and arranged in order to divert light from the viewing angle into a direction that is essentially parallel to the pivot axis of the pivotable prism. The viewing angle and pivot axis in particular form an essentially right angle. Because the viewing angle is indicated in particular by the direction of the distal portion of the optical axis distally from the pivotable prism, and because the pivot axis in particular coincides with the center portion of the optical axis between the two prisms, the distal portion of the optical axis and the center portion of the optical axis in particular form a right angle.

If the pivotable prism includes a level reflecting surface, the angle between the viewing angle and the normals of the reflecting surface and the angle between the normals of the reflecting surface and the pivot axis of the pivotable prism each are equal to 45 degrees. If the reflecting surface of the pivotable prism is curved, the foregoing statement can hold true for the surface normal of the reflecting surface at its point of intersection with the optical axis. In particular, the pivot axis is perpendicular to the longitudinal axis of the endoscope.

The fixed prism is in particular configured and arranged in order to divert light from a direction that is essentially parallel to the pivot axis of the pivotable prism into a direction that is essentially parallel to the longitudinal axis of the endoscope. If the pivot axis of the pivotable prism and the longitudinal axis of the endoscope form an essentially right angle and the fixed prism includes a level reflecting surface, a surface normal of the reflecting surface of the fixed prism can form a 45 degree angle both with the pivot axis of the pivotable prism and with the longitudinal axis of the endoscope. If the reflecting surface of the fixed prism is curved, the foregoing statement can also apply for the surface normal of the reflecting surface at its point of intersection with the optical axis.

In order to move the viewing angle on a conical mantle around the longitudinal axis of the endoscope when there is a given adjustment of the pivotable prism, the entire endoscope with the fixed prism and pivot axis of the pivotable prism can be rotated around its longitudinal axis. Alternatively, the fixed prism together with the pivot axis of the pivotable prism can be rotated with respect to the endoscope around the longitudinal axis of the endoscope. The term "fixed" thus means, in particular, fixed with respect to the pivot axis of the pivotable prism. The fixed prism, in particular, stays fixed with respect to the endoscope, but alternatively it can, as described, be rotatable with the pivot axis of the pivotable prism around the longitudinal axis of the endoscope.

The term "prism" designates a transparent body that comprises a light inlet surface, at least one reflecting surface and a light outlet surface, but one that must not necessarily comprise precisely the shape of a prism in the strict geometric sense. The light inlet surface, the reflecting surface and the light outlet surface of the prism can each be level, such that the normals of the light inlet surface, reflecting surface and light outlet surface lie in a plane or are linearly dependent. The normal of the light inlet surface, the normal of the reflecting surface and the normal of the light outlet surface, however, are not required to lie in one plane.

In addition, the light inlet surface as well as the reflecting surface and light outlet surface can each be curved in order to integrate in one structural element the light-diverting property of the reflecting surface with an imaging property of one or more curved border surfaces.

In addition, a prism in the sense of the foregoing description can comprise two or more reflecting surfaces. The reflection on a reflecting surface of a prism is based in particular, in each case, on total reflection or on a reflecting coating of a surface of the prism.

Embodiments of the endoscope described here can yield numerous additional advantages. In particular, extreme viewing angles and extreme viewing angle ranges can be achieved that easily extend beyond 180 degrees. This is especially true, as mentioned, when the pivot axis of the pivotable prism is perpendicular to the longitudinal axis of the endoscope. In addition, especially large visual fields can be achieved. In particular, a visual field angle or instantaneous field of view of 70 degrees or greater can be achieved. In addition, with embodiments of the endoscope described here, particularly high image qualities and especially bright images are possible.

In an endoscope as described here, a reflecting surface of the fixed prism can be greater than a reflecting surface of the pivotable prism.

In particular, the ratio between the area or diameter of the reflecting surface of the fixed prism and the area or corresponding diameter of the reflecting surface of the pivotable prism can be at least 4:3 or at least 3:2 or at least 2:1.

Alternatively, in an endoscope as described here, a reflecting surface of the pivotable prism can be greater than a reflecting surface of the fixed prism.

In particular, the ratio between the area or diameter of the reflecting surface of the pivotable prism and the area or corresponding diameter of the reflecting surface of the fixed prism is at least 4:3 or at least 3:2 or at least 2:1.

In an endoscope as described here, a light bundle recorded by the endoscope can comprise a tapering at least either in the area of the pivotable prism or in the area of the fixed prism.

Because of the tapering of the light bundle in the area of the pivotable prism and/or in the area of the fixed prism, the structural space taken up by both prisms can be markedly reduced. As will become clear below on the basis of the description of embodiments, as a result the cross-sections of rod lenses, for example, can be enlarged to transmit light to the proximal end of the endoscope. Because of enlarged cross-sections of rod lenses, the brightness, contrast and sharpness of the recorded image can be improved.

Both the pivotable prism and the fixed prism can individually comprise one or more level or curved reflecting surfaces.

In an endoscope as described here, at least either the pivotable prism or the fixed prism can comprise an imaging property.

In an endoscope as described here, at least either the light inlet surface of the pivotable prism or the light outlet surface of the fixed prism can be curved.

In addition, both the light outlet surface of the pivotable prism and the light inlet surface of the fixed prism can be curved. In particular, the prisms in each case can comprise imaging properties because of curved light inlet surfaces and/or light outlet surfaces as well as because of curved reflecting surfaces. As a result, under some conditions it is possible to dispense with a separate lens. In addition, the described tapering of the light bundle recorded by the endoscope can be supported in the area of at least one of the two prisms.

In an endoscope as described here, a center portion of the optical axis between the pivotable prism and the fixed prism can run essentially perpendicular to the longitudinal axis of the endoscope.

In particular, between the reflecting surface of the pivotable prism and the reflecting surface of the fixed prism, a center portion of the optical axis can run essentially perpendicular to the longitudinal axis of the endoscope.

A center portion of the optical axis between the reflecting surface of the pivotable prism and the reflecting surface of the fixed prism is the line (in particular, a straight line) on which a light beam runs that is running proximally from the reflecting surface of the fixed prism on the optical axis, in particular on the optical axis of the succeeding rod lenses. The optical axis in particular also indicates the direction of the transmitted light bundle. As already mentioned, the pivot axis of the pivotable prism can also be perpendicular to the longitudinal axis of the endoscope and thus in particular parallel to the center portion of the optical axis.

In particular, when both the center portion of the optical axis between the reflecting surfaces of the prisms and the pivot axis of the pivotable prism are positioned perpendicular to the longitudinal axis of the endoscope, as already mentioned, especially large viewing angle ranges can result.

In particular with the described tapering of the light bundle recorded by the endoscope in the area of the pivotable prism or in the area of the fixed prism, it becomes possible to achieve an especially small distance between them and thus an especially small lateral displacement between the distal portion of the optical axis distally from the pivotable prism and the proximal portion of the optical axis proximally from the fixed prism. As a result, in a given cross-section of the endoscope shaft, especially large cross-sections of rod lenses and especially good brightness, contrast and sharpness of recorded images can be achieved.

An endoscope as described here can, in addition, comprise a device for erecting an image recorded by means of the endoscope.

An image-erecting device is, in particular, a prism or other device with an uneven number of reflecting surfaces, in particular a Schmidt-Pechan prism or a Dove prism, or as possible alternative a double-Dove prism. The total number of reflecting surfaces of the endoscope is selected here, in particular, as even, in order to avoid a laterally reversed image. The device for erecting a recorded image is positioned, in particular, at the proximal end of the endoscope. The endoscope is in particular configured in such a way that, upon pivoting the pivotable prism around its pivot axis, simultaneously the erecting device is rotated, in particular at half rotation speed. The image-erecting device is thus rotated around its optical axis (distally from its first or distal reflecting surface and proximally from the last or proximal reflecting surface).

The device for erecting the image recorded by means of the endoscope makes possible a fixed orientation of the image recorded by means of the endoscope even when there is a pivoting motion of the pivotable prism around its pivot axis.

In a method for recording an image of an object by means of an endoscope, a pivotable prism is pivoted in relation to an endoscope in order to select a viewing angle of the endoscope. A light emerging from the object is diverted by means of the pivotable prism, so that light diverted by the pivotable prism at least either emerges out of the pivotable prism through a light outlet surface of the pivotable prism that is positioned in a recess of a fixed prism, or enters the fixed prism through a light inlet surface of the fixed prism that is positioned in a recess of the pivotable prism. Light diverted by means of the pivotable prism is diverted by means of a fixed prism in a direction that is essentially parallel to the longitudinal axis of the endoscope shaft. Light diverted by means of the fixed prism is acquired in order to record the image.

The described method can be performed in particular with embodiments of the endoscope described here. The aforementioned advantages are possible as a result.

BRIEF DESCRIPTION OF THE DRAWINGS

Hereinafter, embodiments are presented on the basis of appended drawings, which are as follows.

DETAILED DESCRIPTION OF THE INVENTION

Figure 1:
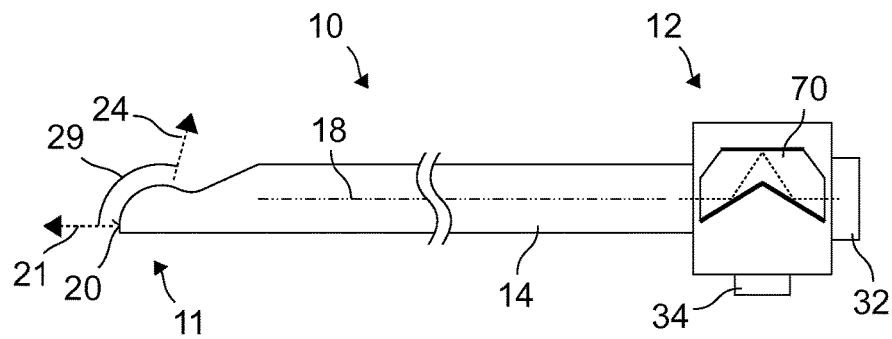
FIG. 1 shows a schematic depiction of an endoscope with adjustable viewing angle.

FIG. 1 shows a schematic depiction of an endoscope 10 with a distal end 11, a proximal end 12 and a rigid shaft 14 that extends from the distal end 11 to the proximal end 12. Alternatively, the shaft 14 can be flexible or partly flexible. The cross-section of the shaft 14 or at least the outer contour of the cross-section of the shaft 14 is constant or essentially constant between the distal end 11 and the proximal end 12. In particular, the contour of the cross-section of the shaft 14 is circular or elliptical. In this case the longitudinal axis 18 of the endoscope 10 shown in FIG. 1 is the axis of symmetry of the mantle surface of the shaft 14 between the distal end 12 and the proximal end 11. In a cylindrical mantle surface of the shaft 14, the longitudinal axis 18 is also the set of the center points or centroids of the cross-section of the shaft 14 between the distal end 12 and the proximal end 11.

On the distal end 12, the shape of the shaft 14 departs from cylindrical symmetry, as is shown by way of example in FIG. 1. In particular, the shaft 14 comprises on the distal end 12 an opening that is closed by a transparent window component with a vaulted surface 20, in particular with a hermetical insulation. The surface 20 of the window component has the shape, for example, of a segment of a cylindrical mantle, such that the axis of symmetry of the cylinder is perpendicular to the longitudinal axis 18 of the endoscope 10 and to the plane of projection of FIG. 1. Alternatively, the surface 20 of the transparent window component has the shape of a segment of a spherical surface or of a two- or three-axis ellipsoid.

On the distal end 12 of the endoscope 10, optical devices are positioned in the shaft 14 that are not shown in FIG. 1. These optical devices, which are described below with reference to FIGS. 2 through 8, make possible a variation of the viewing angle of the endoscope between a first extreme viewing angle 21 and a fourth extreme viewing angle 24. A second and third viewing angle, situated between the first viewing angle 21 and the fourth viewing angle 24, are described hereinafter with reference to FIGS. 3 and 4. The viewing angle in each case is the direction based on the distal end 12 of the endoscope 10 in which an object is situated that appears in the center of an image recorded by means of the endoscope 10.

In the example illustrated in FIG. 1, the first extreme viewing angle 21 is parallel or essentially parallel to the longitudinal axis 18 of the endoscope 10. Between the extreme viewing angles 21, 24 there lies a solid angle 29, which in the illustrated example spans about 120 degrees. Within this solid angle, the viewing angle of the endoscope 10 is, in particular, continually displaceable or adjustable.

On the proximal end 11 the endoscope 10 comprises a first coupling 32 for optical coupling of the endoscope 10 with a video camera or an eyepiece as well as a second coupling 34 for coupling the endoscope 10 with a light source via a light conductor cable. In addition, on its proximal end 11 the endoscope 10 comprises a device 70 for erecting an image recorded by means of the endoscope 10. Without the device 70, in the embodiments presented with reference to FIGS. 2 through 8, a variation of viewing angle in a plane would lead not just to a sliding of the recorded image but also to its rotation. To compensate for the rotation, the device 70 is equipped with an uneven number of reflecting surfaces. A device, not described in further detail here, ensures that in a variation of the viewing angle of the endoscope 10, the device 70 is simultaneously rotated around the longitudinal axis 18 of the endoscope or around an axis parallel thereto, in such a way that the recorded image does not rotate. In particular, a device is provided that, in a pivoting of the pivotable prisms presented hereinafter with reference to FIGS. 2 through 8 by an angle, causes rotation of the device 70 through half of the angle.

Figure 2:
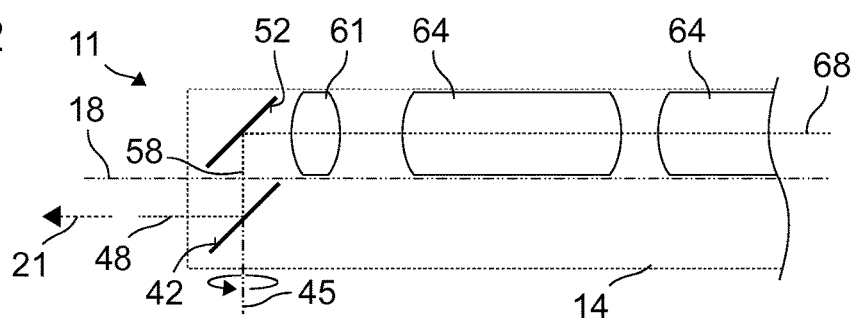
FIG. 2 shows a schematic depiction of an embodiment of the distal end of an endoscope.
Figure 3:
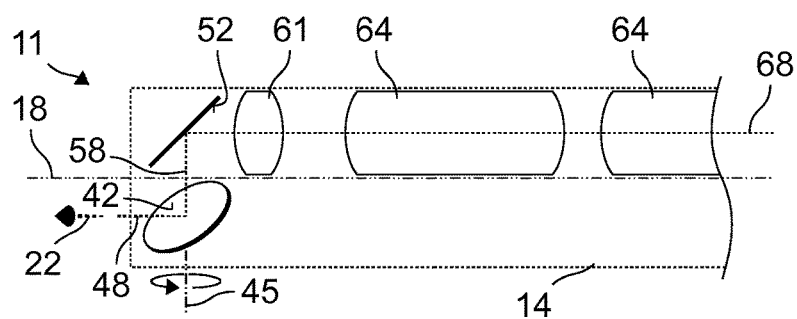
FIG. 3 shows an additional schematic depiction of the embodiment from FIG. 2.
Figure 4:
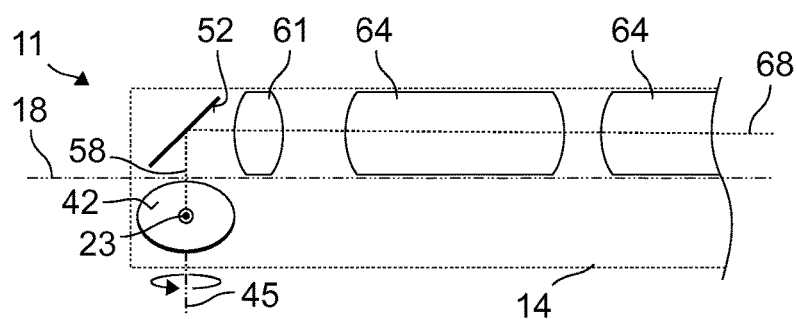
FIG. 4 shows an additional schematic depiction of the embodiment from FIGS. 2 and 3.

FIGS. 2 through 4 show schematic depictions of the distal end of an endoscope with adjustable viewing angle, in particular of the endoscope 10 described above with reference to FIG. 1. The planes of projection of FIGS. 2 through 4 are each parallel to the longitudinal axis 18 of the endoscope 10 and perpendicular to the plane of projection of FIG. 1. The wall of the shaft 14 in each case is indicated only schematically by a rectangular pointed line. The opening and the window component, described above, are not shown in FIGS. 2 through 4 for the sake of clarity. Devices for transmitting or conducting illuminating light in the shaft 14, devices for pivoting the subsequently described pivotable prisms, and other details are likewise not shown in FIGS. 2 through 4 for the sake of a clear presentation.

The endoscope presented in FIGS. 2 through 4 comprises a pivotable reflecting surface 42 and a fixed reflecting surface 52, which in the illustrated example are both level. The reflecting surfaces 42, 52 are each shown by way of example as circular.

The pivotable reflecting surface 42 can pivot or rotate around a pivot axis 45. The pivot axis 45 is perpendicular to the longitudinal axis 18 of the endoscope, perpendicular to the plane of projection of FIG. 1, and parallel to the plane of projection of FIGS. 2 through 4. An angle of approximately 45 degrees in each case is situated between the surface normals of the pivotable reflecting surface 42 and the fixed reflecting surface 52 on the one hand, and the pivot axis 45 of the pivotable reflecting surface 42 on the other hand. The surface normal of the fixed reflecting surface 52 is parallel to the plane of projection of FIGS. 2 through 4.

Connected proximally to the fixed reflecting surface 52 are a line 61 and several rod lenses 64 for transmitting light to the proximal end of the endoscope. Instead of a single lens 61, a group of lenses or an object lens can be provided.

FIGS. 2, 3 and 4 show the pivotable reflecting surface 42 in the various angle positions corresponding to three different viewing angles 21, 22 and 23.

In the orientation of the pivotable reflecting surface 42 illustrated in FIG. 2, the surface normal of the pivotable reflecting surface 42 is parallel to the plane of projection of FIG. 2. The viewing angle corresponds to the first, extreme viewing angle 21, parallel to the longitudinal axis 18 of the endoscope 10, shown in FIG. 1.

In FIG. 3 the pivotable reflecting surface 42 is illustrated in an orientation that is rotated by 45 degrees around the pivot axis 45 with reference to the orientation described above with reference to FIG. 2. The second viewing direction 22, which is thereby produced, forms an angle of 45 degrees in each case, both with the longitudinal axis 18 of the endoscope 10 and with the normals of the plane of projection of FIG. 3.

In the orientation of the reflecting surface 42 shown in FIG. 4, said orientation is rotated around the pivot axis 45 by 90 degrees with respect to the orientation presented above with reference to FIG. 2 and by an additional 45 degrees with respect to the orientation described above with reference to FIG. 3. The resulting third viewing angle 23 is perpendicular to the plane of projection of FIG. 4.

The distal portion 48 of the optical axis distally from the pivotable reflecting surface 42 is also shown in FIGS. 2 and 3. Shown in each of FIGS. 2 through 4, in addition, are the center portion 58 of the optical axis between the reflecting surface 42, 52 and the proximal portion 68 of the optical axis proximally from the fixed reflecting surface 52. The proximal portion 68 of the optical axis proximally from the fixed reflecting surface 52 in this example is simultaneously the optical axis of the lens 61 and the optical axis of the rod lenses 64. The optical axes of the lens 61 and of the rod lenses 64 are in particular axes of symmetry in relation to which the lens 61 or the rod lenses 64 comprise a rotation symmetry.

In the image of geometric or radiant optics, a light beam that emanates from an object situated in the viewing angle 21, 22, 23 and runs proximally from the fixed reflecting surface 52 along the proximal portion 68 of the optical axis, runs distally from the pivotable reflecting surface 42 on the distal portion 48 of the optical axis and between the reflecting surfaces 42, 52 on the proximal portion 48 of the optical axis 58. Thus the distal portion 48 and the center portion 58 of the optical axis intersect at a point, in particular in the center point, of the pivotable reflecting surface 42 and the center portion 58 and proximal portion 68 of the optical axis at a point, in particular in the center point, of the fixed reflecting surface 52.

Light falling from the viewing angle 21, 22 or 23 or from a predetermined solid angle around this viewing angle 21, 22 or 23 on the pivotable reflecting surface 42 is partly, primarily or completely diverted to the fixed reflecting surface 52. From the fixed reflecting surface 52, the light is partly or completely diverted to the lens 61 and transmitted by the lens 61 and the rod lenses 64 to the proximal end 11 of the endoscope 10, in order to generate on an eyepiece there, for example in a video camera or on the retina of a human eye, a real image of the object from which the light emanates. The predetermined solid angle in which objects are situated, viewed from the distal end 12 of the endoscope, and from which an image is generated by the endoscope 10 on its proximal end 11, is also designated as the visual field.

It can be recognized from a comparison of FIGS. 2 through 4 that the viewing angle 21, 22, 23 of the endoscope 10 can be adjusted in a great solid angle 29 by pivoting the reflecting surfaces 42 around the pivot axis 45. The size of the pivot area of the pivotable reflecting surface 42, and the corresponding size of the solid angle 29 within which the viewing angle 21, 22, 23, 24 can be adjusted, are not restricted, or not substantially so, by the optical elements 42, 52, 61 in the embodiment illustrated in FIGS. 2 through 4. In a corresponding configuration of the distal end 12 of the endoscope 10 and in particular of the opening that is positioned there and closed off by a transparent window component, viewing angles can be achieved in solid angles that, starting from a viewing angle 21 parallel to the longitudinal axis 18 of the endoscope 10, can span without doubt more than 90 degrees or even 120 degrees or more in one direction or in two opposite directions. At the same time, visual fields can be achieved with an angle of 70 degrees or more.

FIGS. 5 through 8 show schematic depictions of embodiments of the distal end of an endoscope with adjustable viewing angle, in particular of the endoscope 10 presented above with reference to FIG. 1. The planes of projection of FIGS. 5 through 8 correspond to the planes of projection of FIGS. 2 through 4, and are therefore again parallel to the longitudinal axis of the endoscope 10 and perpendicular to the plane of projection of FIG. 1. FIGS. 5 through 8 also correspond to FIGS. 2 through 4 concerning the depiction of the shaft 14 (in particular without opening and window component) reduced to essentials for the following commentary and the absence of illustration for devices to generate or transmit illuminating light as well as mechanical devices for pivoting the prisms described hereafter.

Contrary to FIGS. 2 through 4, however, in FIGS. 5 through 8 only the first, extreme viewing angle 21 is shown in each case. It was decided, for the sake of brevity, to dispense with an illustration of the pivotable prisms described hereafter in orientations that correspond to other viewing angles. It is obvious for the specialist, however, how the pivotable prisms described hereafter can be pivoted around their pivot axes in order to select other viewing angles. In particular, the prisms can be pivoted in ways corresponding to those presented above with reference to FIGS. 2 through 4 for the reflecting surface 42.

In the embodiments presented in FIGS. 5 through 8, the reflecting surfaces 42, 52 are each a component of a pivotable prism 40 or of a fixed prism 50. In each of the embodiments presented in FIGS. 5 through 8, the pivotable prism 40 also comprises a light inlet surface 41 and a light outlet surface 43. In each of the embodiments presented in FIGS. 5 through 8, the fixed prism 50 also comprises a light inlet surface 51 and a light outlet surface 53.

The light inlet surface 41 of the pivotable prism 40 in each case faces the viewing angle 21, so that in particular, at least on the distal portion 48 of the optical axis, the surface normal of the light inlet surface 41 is parallel to the viewing angle 21. The light outlet surface 43 of the pivotable prism 40 and the light inlet surface 51 of the fixed prism 50 are facing one another, so that in particular, at least on the center portion 58 of the optical axis between the reflecting surfaces 42, 52, the surface normals of the light outlet surface of the pivotable prism 43 and the light inlet surface 51 of the fixed prism 50 are antiparallel to one another. The light outlet surface 53 of the fixed prism 50 faces the lens 61 in each case, so that in particular, at least on the proximal portion 68 of the optical axis, the surface normal of the light outlet surface 53 is parallel to the proximal portion 68 of the optical axis.

The embodiments depicted in FIGS. 5 through 8 differ with respect to the sizes and shapes of the pivotable prisms 40 and of the fixed prisms 50.

Figure 5:
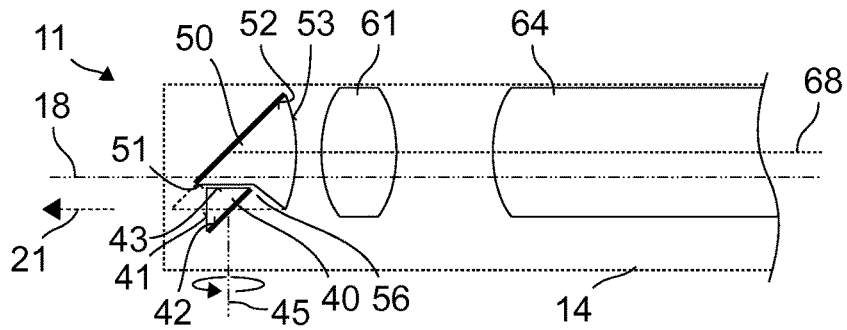
FIG. 5 shows a schematic depiction of an additional embodiment of the distal end of an endoscope.

In the embodiment shown in FIG. 5, the reflecting surface 52 of the fixed prism 50 is greater than the reflecting surface 42 of the pivotable prism 40. In particular, the linear dimensions or the surface areas of the reflecting surface 52 of the fixed prism 50 and of the reflecting surface 42 of the pivotable prism 40 have a ratio of at least 4:3 or at least 3:2 or at least 2:1. Alternatively, both reflecting surfaces 42, 52 can be of the same size or essentially of the same size, contrary to the illustration in FIG. 5.

In addition, the light outlet surface 53 of the fixed prism 50 is curved, in particular convexly curved. Alternatively the light outlet surface 53 of the fixed prism 50 can be level, departing from the illustration in FIG. 5.

In addition, the pivotable prism 40 is positioned at least partly in a recess 56 of the fixed prism 50. In particular, the light outlet surface 43 of the pivotable prism is positioned in the recess 56 of the fixed prism 50. The recess 56 is clearly recognizable, especially in comparison to the contour of a fixed prism 50 without recess that is depicted in an interrupted line. The light inlet surface 51 of the fixed prism 50 forms a partial area of the surface of the fixed prism 50 lying inside the recess 56.

The partial area of the surface of the fixed prism 50 lying in the recess 56 is altogether concave or essentially concave and includes smaller level portions. In particular, the light inlet surface 51 of the fixed prism 50 is level. Alternatively, the partial area of the surface of the fixed prism 50 situated in the recess 56 can include small locally convex portions. For example, the light inlet surface 51 of the fixed prism 50, contrary to the depiction in FIG. 5, can be convex. The overall concave property of the partial area of the surface of the fixed prism 50 situated in the recess 56 is, in particular, recognizable in the plane of intersection depicted in FIG. 5.

In the example illustrated in FIG. 5, the recess 56 is characterized in addition in that part of the fixed prism 50, in particular a part of the light outlet surface 53 of the fixed prism 50, overlaps or extends out beyond a plane in which the light inlet surface 51 is situated.

Figure 6:
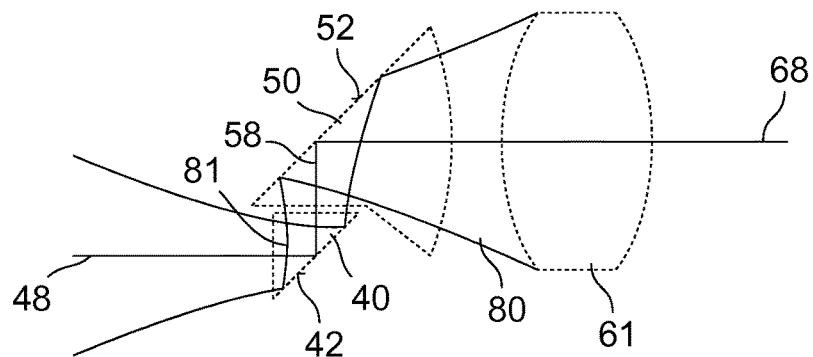
FIG. 6 shows a schematic depiction of the beam path in the embodiment from FIG. 5.

FIG. 6 shows an enlarged view of a portion of the embodiment illustrated in FIG. 5. The prisms 40, 50 and the lens 61 are indicated only in interrupted outline. A light bundle 80 from the visual field is shown in hatched lines. The light bundle 80 is diverted to the lens 61 by means of the reflecting surfaces 42, 52 of the pivotable prism 40 or of the fixed prism 50. The prisms 40, 50 and the lens 61 as well as, in some cases, one or more lenses distally from the pivotable prism 40 that are not shown in FIGS. 5 and 6 are configured so that the light bundle 80 comprises an indentation or tapering 81 in the area of the pivotable prism 40. This tapering 81 of the light bundle 80 can contribute toward making possible a pronounced difference in size between the reflecting surface 42 of the pivotable prism 40 on the one hand and the reflecting surface 52 of the fixed prism and of the cross-section surface of the light bundle 80 proximally from the fixed prism on the other hand.

Figure 7:
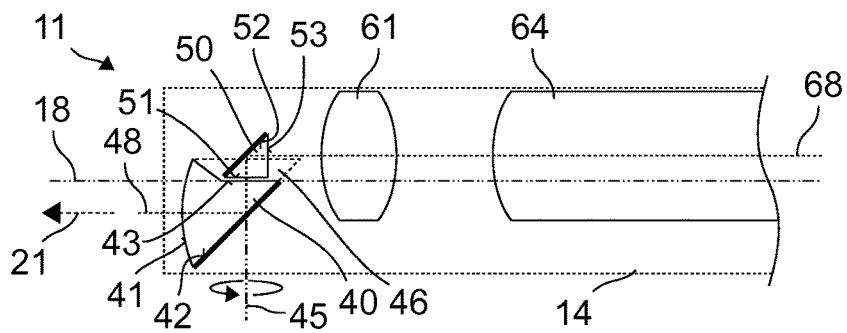
FIG. 7 shows a schematic depiction of an additional embodiment of the distal end of an endoscope.

FIG. 7 shows a schematic view of an embodiment that is distinguished in part from the embodiment presented above with reference to FIG. 5 in that the pivotable prism 40 and the reflecting surface 42 of the pivotable prism 40 are greater or markedly greater than the fixed prism 50 or its reflecting surface 52.

In addition, the embodiment shown in FIG. 7 differs from the embodiment presented above with reference to FIG. 5 in that the fixed prism 50 is positioned partly in a recess 46 of the pivotable prism 40. In particular, the light inlet surface 51 of the fixed prism 50 is positioned in the recess 46 of the pivotable prism 40. The light outlet surface 43 of the pivotable prism 40 forms a partial area of the surface of the pivotable prism 40 in the recess 46. The recess 46 can be recognized especially in comparison to the contour of a pivotable prism without recess that is depicted in interrupted outline.

In addition, the embodiment shown in FIG. 7 is distinguished from the embodiment described above with reference to FIG. 5 in that the light inlet surface 41 of the pivotable prism 40 is curved, in particular convex. Alternatively the light inlet surface 41 of the pivotable prism 40 can be level or concave, contrary to the illustration in FIG. 7.

In the embodiment shown in FIG. 7, a light bundle directed by the reflecting surfaces 42, 52 of the prisms 40, 50 onto the lens 61 in the area of the fixed prism 50 comprises an inlet or tapering. The light bundle and its tapering are not shown in FIG. 7 but they are similar to those shown in FIG. 6.

Figure 8:
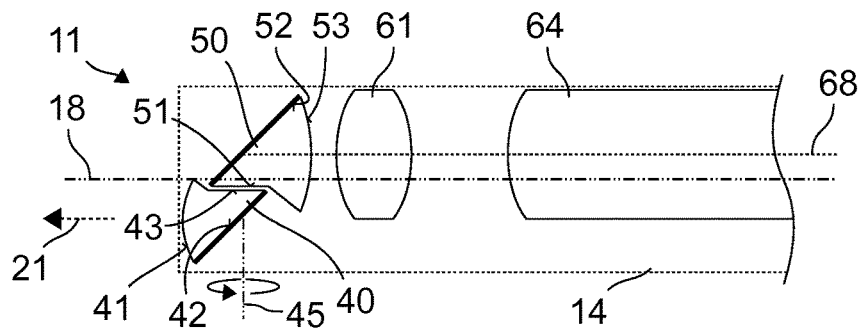
FIG. 8 shows a schematic depiction of an additional embodiment of the distal end of an endoscope.

FIG. 8 shows a schematic depiction of an embodiment that is distinguished from the embodiments described above with reference to FIGS. 5 through 7 in that both the pivotable prism 40 and the fixed prism 50 comprise a recess. Because these recesses are clearly recognizable for specialists in FIG. 8 also, after the foregoing descriptions with reference to FIGS. 5 through 7, reference numbers were dispensed with in the interest of simplicity of presentation.

The embodiment shown in FIG. 8 is distinguished further from the embodiments presented above with reference to FIGS. 5 through 7 in that both the light inlet surface 41 of the pivotable prism 40 and the light outlet surface 53 of the fixed prism 50 are curved or vaulted. Alternatively, the light inlet surface 41 of the pivotable prism 40 and the light outlet surface 53 of the fixed prism 50 can each be level or bent in concave manner.

The pivotable prism 40 in the embodiment presented with reference to FIG. 8 is smaller than the fixed prism 50. Alternatively, contrary to the depiction in FIG. 8, both prisms 40, 50 can be equally large or the pivotable prism 40 can be greater than the fixed prism 50.

Contrary to the depictions in FIGS. 2 through 8, even in the embodiments presented with reference to FIGS. 2 through 8 the reflecting surfaces 42, 52 can be curved in convex or concave manner. In addition, the light inlet surfaces 41, 51 and light outlet surfaces 43, 53 that are shown as level in FIGS. 5 through 8 can also be curved in convex or concave manner. Because of curved light inlet surfaces 41, 51, curved reflecting surfaces 42, 52 and curved light outlet surfaces, the prisms 40, 50 can comprise not only light-diverting properties but simultaneously imaging properties (in particular, generation of real or virtual images) and can support the tapering of the light bundle presented above with reference to FIGS. 6 through 8 and especially with reference to FIG. 7. In addition, both the pivotable prism 40 and the fixed prism 50 can comprise several reflecting surfaces, for example in the form of a pentaprism or a roof pentaprism.

Figure 9:
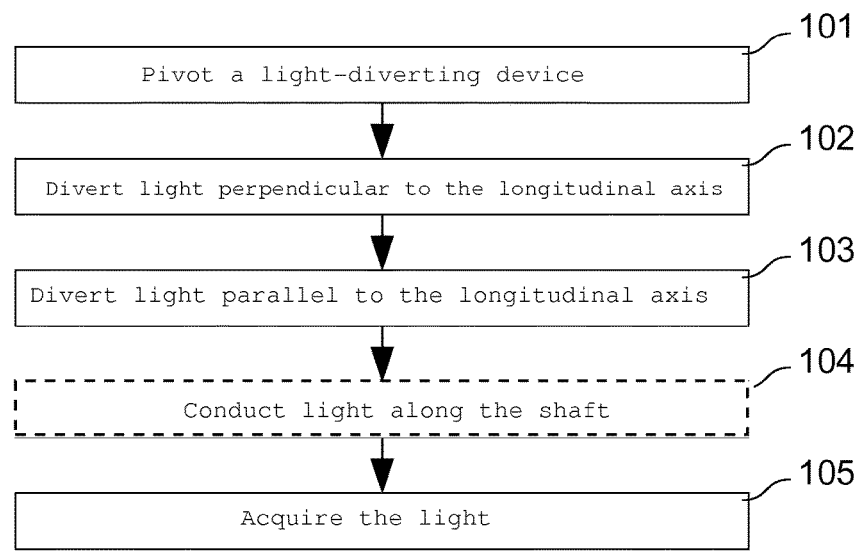
FIG. 9 shows a schematic flow diagram of a method for recording an image by means of an endoscope.

FIG. 9 shows a schematic flow diagram of a method for recording an image of an object by means of an endoscope. Although this method can also be performed with an endoscope that differs from the embodiments presented above with reference to FIGS. 1 through 8, hereinafter reference numbers from FIGS. 1 through 8 are used by way of example for the sake of clarity.

In a first step 101, a pivotable prism 40, 42 is pivoted in order to select a viewing angle of the endoscope 10. The prism is pivoted around a pivot axis 45 that is, in particular, perpendicular to the longitudinal axis of the endoscope. The viewing angle is adjusted in particular to an object that is to be observed or essentially to the object that is to be observed. The steps described hereinafter can be performed simultaneously with the first step 101.

In a second step 102, light from a viewing angle 21, 22, 23, 24 adjusted by pivoting of the pivotable prism 40 is diverted into a direction essentially parallel to the pivot axis 45. This occurs, in particular, by means of a reflecting surface 42 of the prism 40. Light diverted by the pivotable prism 40 emerges through a light outlet surface 43 of the pivotable prism 40, which is positioned in a recess 56 of a fixed prism 50, out of the pivotable prism 40. Alternatively or in addition, light diverted by the pivotable prism 40 enters through a light inlet surface 51 of the fixed prism 50, which is positioned in a recess 46 of the pivotable prism 40, into the fixed prism 50.

In a third step 103, light that spreads essentially parallel to the pivot axis 45 of the pivotable prism 40 is diverted into a direction that is essentially parallel to the longitudinal axis 18 of the endoscope 10. This occurs in particular by means of a reflecting surface 52 of the prism 50. In an optional fourth step 104, light diverted in the second step 102 and in the third step 103 is conducted along the shaft 14 of the endoscope 10 to the proximal end 11 of the endoscope 10. In a fifth step 105, light that was diverted in the second step 102 and in the third step 103 and that was optionally conducted in the fourth step 104 to the proximal end 11 of the endoscope 10, is acquired. Thus an image of the object from which the light emerges is recorded by means of a video camera or by means of an eyepiece and the human eye.

What is claimed is:

1. An endoscope with adjustable viewing angle, said endoscope comprising:
   a pivotable prism to divert light, said pivotable prism being pivotable around a pivot axis to adjust the viewing angle, the pivotable prism having a single reflecting surface; and
   a fixed prism to divert light that is diverted by the pivotable prism into a direction parallel to a longitudinal axis of the endoscope, the fixed prism having a single reflecting surface;
   wherein at least one of a light outlet surface of the pivotable prism is positioned in a recess of the fixed prism or a light inlet surface of the fixed prism is positioned in a recess of the pivotable prism; and
   wherein at least a portion of the recess of the fixed prism includes a level surface in an area of the recess that is aligned with the light outlet surface of the pivotable prism, or a portion of the recess of the pivotable prism includes a level surface in an area of the recess that is aligned with the light inlet surface of the fixed prism.

2. The endoscope according to claim 1, wherein an area of a reflecting surface of the fixed prism is greater than an area of a reflecting surface of the pivotable prism.

3. The endoscope according to claim 1, wherein an area of a reflecting surface of the pivotable prism is greater than an area of a reflecting surface of the fixed prism.

4. The endoscope according to claim 1, wherein a light bundle transmitted by the endoscope tapers in at least one of the area of the pivotable prism or the area of the fixed prism.

5. The endoscope according to claim 1, wherein at least one of the pivotable prism or the fixed prism comprises one or more curved surfaces.

6. The endoscope according to claim 5, wherein said one or more curved surfaces provide generation of at least one of real or virtual images.

7. The endoscope according to claim 1, wherein at least one of the light inlet surface of the pivotable prism or the light outlet surface of the fixed prism is curved.

8. The endoscope according to claim 1, wherein a center portion of the optical axis runs between the pivotable prism and the fixed prism essentially perpendicular to the longitudinal axis of the endoscope.

9. The endoscope according to claim 1, wherein the level surface of the recess of the fixed prism and the light outlet surface of the pivotable prism are aligned with the longitudinal axis of the endoscope.

10. The endoscope according to claim 1, wherein the light inlet surface of the fixed prism is positioned in the recess of the pivotable prism; and
    the portion of the recess of the pivotable prism includes the level surface in the area of the recess that is aligned with the light inlet surface of the fixed prism.

11. The endoscope according to claim 1, wherein a ratio of a surface area of the single reflecting surface of the pivotable prism to a surface area of the single reflecting surface of the fixed prism is at least 2:1.

12. The endoscope according to claim 1, wherein the fixed prism has a convex light outlet surface formed as a unitary feature of the fixed prism.

13. The endoscope according to claim 1, wherein the pivotable prism has a convex light inlet surface.

14. The endoscope according to claim 1, wherein both the pivotable prism and the fixed prism are enclosed within a shaft.

15. The endoscope according to claim 1, wherein the recess of the fixed prism is configured to receive the pivotable prism within the recess of the fixed prism, or the recess of the pivotable prism is configured to receive the fixed prism within the recess of the pivotable prism.

16. A method of viewing an image of an object using an endoscope, said method comprising the following steps:
    pivoting a pivotable prism with respect to the endoscope in order to adjust a viewing angle of the endoscope, the pivotable prism having a single reflecting surface;
    diverting light that emerges from the object by means of the pivotable prism, such that light diverted by the pivotable prism at least either emerges through a light outlet surface of the pivotable prism, which is positioned in a recess of a fixed prism, out of the pivotable prism or enters through a light inlet surface of the fixed prism, which is positioned in a recess of the pivotable prism, into the fixed prism;
    diverting light that is diverted by means of the pivotable prism by means of the fixed prism into a direction that is essentially parallel to a longitudinal axis of a shaft of the endoscope, the fixed prism having a single reflecting surface;
    acquiring light that has been diverted by means of the pivotable prism and the fixed prism using a reflecting surface of the fixed prism in order to transmit the image to at least one of a camera or eyepiece coupled to the endoscope
    wherein at least a portion of the recess of the fixed prism includes a level surface in an area of the recess that is aligned with the light outlet surface of the pivotable prism, or a portion of the recess of the pivotable prism includes a level surface in an area of the recess that is aligned with the light inlet surface of the fixed prism.

17. The method according to claim 16, wherein light emerging from the object is diverted by means of a reflecting surface of the pivotable prism that is smaller than the reflecting surface of the fixed prism.

18. The method according to claim 16, wherein light emerging from the object is diverted by means of a reflecting surface of the pivotable prism that is greater than the reflecting surface of the fixed prism.

* * * * *